United States Patent [19]

Ohno et al.

[11] Patent Number: 4,508,817
[45] Date of Patent: Apr. 2, 1985

[54] METHOD OF COLOR PHOTOGRAPHIC PROCESSING

[75] Inventors: Shigeru Ohno; Shinzo Kishimoto, both of Kanagawa, Japan

[73] Assignee: Fuji Photo Film Co., Ltd., Kanagawa, Japan

[21] Appl. No.: 612,173

[22] Filed: May 21, 1984

[30] Foreign Application Priority Data

May 20, 1983 [JP] Japan ................................ 58-88938

[51] Int. Cl.$^3$ ................................................ G03C 7/00
[52] U.S. Cl. .................................... 430/393; 430/429; 430/430; 430/460; 430/461
[58] Field of Search ............... 430/393, 429, 430, 460, 430/461

[56] References Cited

U.S. PATENT DOCUMENTS 3,748,136  7/1973  Willems .............................. 430/461
3,870,520  3/1975  Shimamura et al. ................ 430/393
4,163,669  8/1979  Kanada et al. ...................... 430/393
4,446,225  5/1984  Kishimoto et al. ................. 430/393

FOREIGN PATENT DOCUMENTS 1458197  12/1976  United Kingdom .

Primary Examiner—J. Travis Brown
Attorney, Agent, or Firm—Sughrue, Mion, Zinn, Macpeak and Seas

[57] ABSTRACT

A method of color photographic processing is disclosed. The method comprises color developing an exposed silver halide color photographic light-sensitive material and thereafter carrying out a bleach treatment and a fix treatment or a bleach-fix treatment, wherein the bleaching agent used for the bleach treatment or the bleach-fix treatment is a ferric ion complex salt or a persulfate and the bleaching bath or the bleach-fixing bath or a pre-bath therefor contains at least one compound represented by the following formula (I):

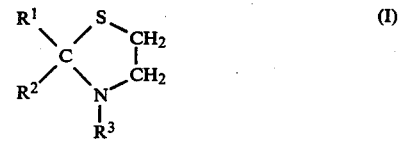

wherein all the symbols are defined in the specification. A prevention of pollution problems and an acceleration of bleaching action without deterioration of photographic properties can be attained by this method.

10 Claims, No Drawings

METHOD OF COLOR PHOTOGRAPHIC PROCESSING

FIELD OF THE INVENTION

The present invention relates to a method of processing silver halide color photographic light-sensitive materials (hereinafter, referred to as "color light-sensitive materials") which comprises developing, bleaching and fixing an exposed silver halide color photographic light-sensitive material (hereinafter, referred to as a "method of color photographic processing") and, particularly, to an improved method of bleach treatment, by which color photographic images having good image quality can be formed by accelerating bleaching action to shorten the processing time and to carry out sufficient bleaching.

BACKGROUND OF THE INVENTION

Generally, the fundamental steps for processing color light-sensitive materials are a color development step and a desilvering step. Namely, an exposed silver halide color photographic material is processed in a color development step. In this step, silver halide is reduced by a color developing agent to form silver and, at the same time, the oxidized color developing agent reacts with color couplers to form dye images. Thereafter, the color photographic material is processed in a desilvering step. In this step, silver formed in the prior step is oxidized by the action of an oxidizing agent (which is generally called a bleaching agent) and thereafter it is removed by dissolving with a complexing agent for silver ions which is generally called a fixing agent. Consequently, only dye images are present in the photographic materials processed by these steps. Practical development processing includes auxiliary steps for keeping good photographic or physical quality of the images or for improving storage stability of the images in addition to the above described fundamental steps of color development and desilvering. For example, a hardening bath for preventing excessive softening of light-sensitive layers during processing, a stopping bath for effectively stopping the development reaction, an image stabilizing bath for stabilizing the images and a defilming bath for removing the backing layer on the support are known auxiliary steps.

Further, with respect to the above described desilvering step, two approaches exist, namely, the two steps wherein the bleaching bath and the fixing bath are separate from each other and one step wherein the bleach-fixing bath containing a bleaching agent and a fixing agent is used in order to further simplify the processing for the purpose of rapid treatment and reduction of labor.

Potassium ferricyanide and ferric chloride used hitherto as bleaching agents are excellent from the standpoint of the large oxidizing power they possess. However, since bleaching solutions or bleach-fixing solutions using potassium ferricyanide as a bleaching agent release cyanide by photolysis to cause disposal problems, waste liquors containing such should be processed in order to completely remove pollution problems. Further, bleaching solutions using ferric chloride as a bleaching agent have not only the disadvantage that they easily cause apparatus corrosion, because they have a very low pH and a very large oxidizing power, but also the disadvantage that iron hydroxide is precipitated in the emulsion layers in the water wash step after the bleach treatment is carried out with stains arising.

On the other hand, potassium bichromate, quinones and copper salts, etc., have been used hitherto as bleaching agents, but they have disadvantages that they have a low oxidizing power and they are difficult to handle.

In recent years, for rapid simple processing and prevention of environmental pollution, a bleach treatment using ferric ion complex salts (for example, ferric ion complex salts of aminopolycarboxylic acids, etc., and, particularly, ethylenediaminetetraacetato iron (III) complex salts) as main components is utilized for color photographic light-sensitive materials.

However, ferric ion complex salts have a comparatively low oxidizing power and an insufficient bleaching power. Therefore, although the desired object can be attained to some extent by using them in a bleach treatment or bleach-fixing treatment of low speed silver halide color photographic light-sensitive materials comprising silver bromochloride emulsions as the main components, disadvantageously the bleaching action is insufficient resulting in inferior desilvering or a long period of time is required for bleaching in processing spectrally sensitized high speed silver halide color photographic light-sensitive materials comprising silver chlorobromoiodide or silver iodobromide emulsions as the main components, particularly, color reversal light-sensitive materials for photography which contain high silver content emulsions and color negative light-sensitive materials for photography.

Persulfates are known as bleaching agents other than ferric ion complex salts. Persulfates are generally used in a bleaching solution containing chlorides. However, bleaching solutions using persulfates have the disadvantage that the bleaching power is inferior to that of ferric ion complex salts and a very long period of time is required for bleaching.

As described above, bleaching agents which do not cause pollution problems and do not corrode apparatus have an inferior bleaching power. Accordingly, it has been desired to increase the bleaching ability of the bleaching solutions or bleach-fixing solutions using bleaching agents having a poor bleaching power, particularly, ferric ion complex salts and persulfates.

Hitherto, additions of various bleaching accelerators to processing baths in order to increase bleaching ability of the bleaching solutions or bleach-fixing solutions containing a ferric ion complex salt such as iron salt of ethylenediaminetetraacetic acid as a bleaching agent have been proposed. Examples of such bleaching accelerators are, for example, the thiourea derivatives described in Japanese patent publication 8506/70 and U.S. Pat. No. 3,706,561, selenourea derivatives described in Japanese Patent Application (OPI) 280/71 (the term "OPI" as used herein refers to a "published unexamined Japanese patent application"), 5-member ring mercapto compounds described in British Pat. No. 1,138,842, and thiourea derivatives, thiazole derivatives and thiadiazole derivatives described in Swiss Pat. No. 336,257, etc. However, many of these bleaching accelerators do not always show a satisfactory bleach acceleration effect or they have the disadvantage that the useful life of the processing solutions is short and the processing solutions cannot be stored for a long period of time, because they are not stable processing solutions.

Further, a method using 4-carboxythiazolidine derivatives as bleaching accelerators is described in Japanese Patent Publication No. 9854/78. However, these bleaching accelerators have the disadvantage that the useful life in the processing solutions is short, because they have a poor bleach accelerating effect and lack stability as a processing solution.

SUMMARY OF THE INVENTION

A first object of the present invention is to provide a method of color photographic processing which prevents pollution problems because of low toxicity and has excellent bleaching rate.

A second object of the present invention is to provide a method of increasing the bleaching power in a bleach treatment or a bleach-fixing treatment using a bleaching agent having a low bleaching power, particularly, ferric ion complex salts or persulfates, without a deterioration of photographic properties.

A third object of the present invention is to provide a bleaching process using a processing solution having good stability, by which the bleaching rate is increased in the bleaching solution or the bleach-fixing solution.

A fourth object of the present invention is to provide a method by which color photographic light-sensitive materials having, particularly, a photographing sensitivity can be bleached or bleach-fixed rapidly.

The above described objects of the present invention are attained by a method of color photographic processing which comprises color developing an exposed silver halide color photographic light-sensitive material and thereafter carrying out a bleach treatment and fix treatment or a bleach-fix treatment, wherein the bleaching agent used for the bleach treatment or the bleach-fix treatment is a ferric ion complex salt or a persulfate and the bleaching bath or the bleach-fixing bath or a pre-bath therefor contains at least one compound represented by the following formula (I)

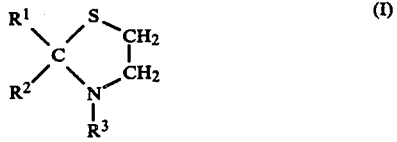

wherein $R^1$ and $R^2$ represent each a hydrogen atom, an alkyl group (preferably having 1 to 20 carbon atoms) which may be substituted, a phenyl group which may be substituted, or a heterocyclic group which may be substituted, and $R^3$ represents a hydrogen atom or a lower alkyl group (preferably having 1 to 3 carbon atoms) which may be substituted.

DETAILED DESCRIPTION OF THE INVENTION

Examples of suitable alkyl groups represented by $R^1$ and $R^2$ include a methyl group, an ethyl group and a butyl group, etc.

Substituents on the alkyl groups represented by $R^1$ and $R^2$ in the above described general formula and the lower alkyl group represented by $R^3$ include a hydroxyl group, a nitro group, a cyano group, a carboxyl group, a sulfonic acid group, an amino group (for example, an unsubstituted amino group and a substituted amino group such as a dimethylamino group, etc.), a halogen atom (for example, a chlorine, bromine and fluorine, etc. atom), a carbamoyl group (for example, an unsubstituted carbamoyl group and a substituted carbamoyl group such as a methylcarbamoyl group, etc.), a sulfamoyl group (for example, an unsubstituted sulfamoyl group and a substituted sulfamoyl group such as a methylsulfamoyl group, etc.), an amido group (for example, an acetylamino group, etc.), a sulfonamido group (for example, a methanesulfonylamino group, etc.), an alkoxy group (for example, a methoxy group and a methoxyethoxy group, etc.), in alkoxycarbonyl group (for example, a methoxycarbonyl group, etc.), a carbonyloxy group (for example, an acetyloxy group, etc.), an alkoxysulfonyl group (for example, a methoxysulfonyl group, etc.), a sulfonyloxy group (for example, a methanesulfonyloxy group, etc.), a sulfonyl group (for example, a methanesulfonyl group, etc.) and a heterocyclic group (for example, a thiazolidinyl group, etc.). Suitable substituents on the phenyl group and the heterocyclic group represented by $R^1$ and $R^2$ include an alkyl group (for example, a methyl group and an ethyl group, etc.) and an aryl group in addition to the above described substituents for the alkyl group. Further, heterocyclic groups represented by $R^1$ and $R^2$ include heterocyclic groups containing at least one hetero atom such as a nitrogen atom, an oxygen atom or a sulfur atom, etc. (and where plural hetero atoms are present, they may be the same or different from each other) and condensed heterocyclic groups.

Suitable heterocyclic groups include those having a 5- or 6-membered ring in which 1 to 4 nitrogen atoms, one oxygen atom and/or one sulfur atom are contained.

Examples of suitable heterocyclic groups include pyridine, thiophene, thiazolidine, benzimidazole, benzothiazole, benzoxazole, benzotriazole, thiazole, imidazole and oxazole, etc.

Examples of suitable lower alkyl groups represented by $R^3$ include a methyl group, an ethyl group, a propyl group, a hydroxyethyl group, a dimethylaminoethyl group, a carboxyethyl group, a sulfopropyl group and a methanesulfonylethyl group, etc.

Compounds which can be suitably used in the present invention of the general formula (I) are those wherein $R^1$ or $R^2$ represents a heterocyclic group and those which are represented by the general formula (II):

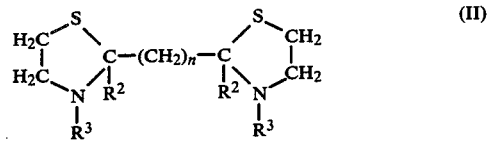

wherein $R^2$ and $R^3$, which may be the same or different, each have the same meaning as described for $R^2$ and $R^3$ in the general formula (I), and n represents 0 or an integer of 1 to 3. Further, it is preferred for $R^2$ to represent a hydrogen atom or an alkyl group which may be substituted. The general formula (II) corresponds to the general formula (I) when $R^1$ represents an alkyl group substituted with a thiazolidinyl group.

Examples of compounds represented by the general formulae (I) and (II) and salts thereof are described below, but the present invention is not to be construed as being limited to these exemplified compounds.

-continued

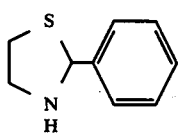

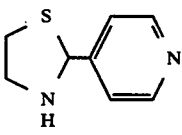

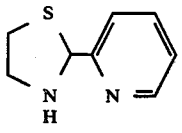

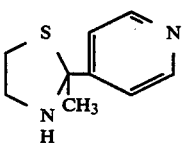

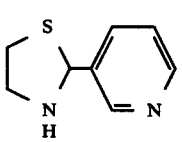

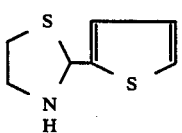

(2)
(3)
(4)
(5)
(6)

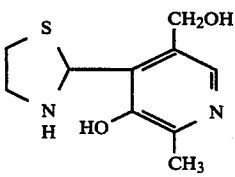

(7)

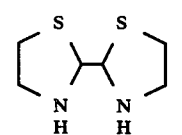

(8)

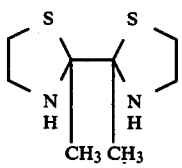

(9)

(10)

(11)

-continued

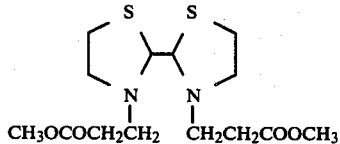 (12)

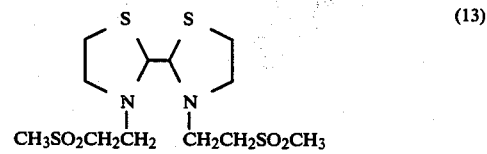 (13)

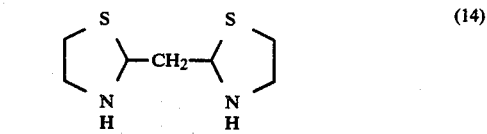 (14)

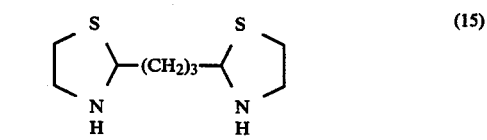 (15)

Thiazolidine derivatives represented by the general formulae (I) and (II) used in the present invention can be synthesized by a condensation reaction between 2-mercaptoethylamines and the corresponding carbonyl compounds. For example, the synthesis is described in H. Jadamus, Q. Fernando, H. Freiser, *Inorganic Chemistry*, 3, 928 (1964).

Typical examples of the synthesis of compounds of the formula (I) are described below, and other compounds can be synthesized in the same manner. Unless otherwise indicated herein, all parts, percents, ratios and the like are by weight.

SYNTHESIS EXAMPLE 1

Synthesis of Compound (2)

11.6 g of 2-aminoethanethiol was dissolved in 120 ml of ethanol, and 16 g of benzaldehyde was added dropwise thereto. After the mixture was refluxed for 1 hour with heating, it was filtered with heating. The filtrate was cooled to precipitate crystals. They were filtered off and recrystallized from ethanol. Yield: 17 g (68%), Melting Point: 108°–109° C.

SYNTHESIS EXAMPLE 2

Synthesis of Compound (3)

11.6 g of 2-aminoethanethiol was dissolved in 120 ml of ethanol, and 16 g of 4-pyridyl aldehyde was added dropwise thereto. After refluxing for 1 hour with heating, the solvent was distilled away and the resulting residue was recrystallized from ethyl acetate. Yield: 13.2 g (53%), Melting Point: 75°–77° C.

SYNTHESIS EXAMPLE 3

Synthesis of Compound (4)

11.6 g of 2-aminoethanethiol was dissolved in 120 ml of ethanol, and 16.1 g of 2-pyridyl aldehyde was added thereto. The mixture was refluxed for 1 hour with heating. After conclusion of the reaction, the solvent was distilled away under a reduced pressure, and the resulting residue was purified by column chromatography

SYNTHESIS EXAMPLE 4

Synthesis of Compound (5)

11.6 g of 2-aminoethanethiol was dissolved in 120 ml of ethanol, and 18.2 g of 4-acetylpyridine was added thereto. The mixture was refluxed for 2 hours with heating. The reacting solution was cooled and the resulting crystals were recrystallized from ethanol. Yield: 7.2 g (4.8%), Melting Point: 157°–159° C.

SYNTHESIS EXAMPLE 5

Synthesis of Compound (6)

11.6 g of 2-aminoethanethiol was dissolved in 120 ml of ethanol, and 16.1 g of 3-pyridyl aldehyde was added thereto. After refluxing for 1 hour with heating, the solvent was distilled away under a reduced pressure. The resulting residue was purified by column chromatography (stationary phase: silica gel, developing solvent: ethyl acetate/chloroform) to obtain a yellow liquid. Yield: 17 g (68%).

SYNTHESIS EXAMPLE 6

Synthesis of Compound (7)

11.6 g of 2-aminoethanethiol was dissolved in 120 ml of methanol, and 16.8 g of 2-thiophenealdehyde was added thereto. The mixture was refluxed for 1.5 hours with heating. After conclusion of the reaction, the solvent was distilled away under a reduced pressure, and the resulting residue was recrystallized from a mixed solvent composed of methanol and water (2:1 by vol). Yield: 16.4 g (64%), Melting Point: 45°–46° C.

SYNTHESIS EXAMPLE 7

Synthesis of Compound (8)

11.6 g of 2-aminoethanethiol was dissolved in 120 ml of methanol, and 16.8 g of 3-thiophenealdehyde was added thereto. The mixture was refluxed for 1.5 hours with heating. After conclusion of the reaction, the solvent was distilled away under a reduced pressure, and the resulting residue was recrystallized from ethanol. Yield: 18.4 g (71%), Melting Point: 91°–92° C.

SYNTHESIS EXAMPLE 8

Synthesis of Compound (9)

10.2 g of pyridoxal hydrochloride was added to 100 ml of ethanol, and a solution of 2.8 g of potassium hydroxide in 30 ml of methanol was added thereto. The formed potassium chloride was filtered out. 3.9 g of aminoethanethiol was added to the filtrate and the mixture was refluxed for 1 hour with heating. After conclusion of the reaction, the solvent was distilled away under a reduced pressure, and the resulting residue was recrystallized from acetone. Yield: 5.7 g (50%), Melting Point: 146°–147° C.

SYNTHESIS EXAMPLE 9

Synthesis of Compound (10)

11.6 g of 2-aminoethanethiol was dissolved in 120 ml of methanol, and 10.9 g of glyoxal (40% aqueous solution) was added dropwise thereto. After refluxing for 5 minutes with heating, the reactant solution was cooled. The formed crystals were filtered off and recrystallized from ethanol. Yield: 6.6 g (50%), Melting Point: 178°–180° C. (decomposition).

Compounds represented by the above described general formula (I) which are bleaching accelerators used in the present invention may be incorporated in a bleach bath or a bleach-fixing bath or may be incorporated in only a pre-bath therefor. Further, they may be incorporated in both the bleach bath or bleach-fixing bath and the pre-bath. The amount of the compounds in the present invention added to these solutions varies depending on the kind of processing solution, the kind of photographic material to be processed, the processing temperature and the time required for processing, etc., but a preferred range is about $1 \times 10^{-5}$ to about 1 mol, preferably $1 \times 10^{-4}$ to $1 \times 10^{-1}$ mol, per liter of processing solution. However, when the amount is small, the bleach accelerating effect is generally small and, when the amount is larger than needed, precipitation occurs to stain the material to be processed. Therefore, it is preferred to determine suitably an optimum range according to each case.

In order to add the compounds of the present invention to the processing solutions, they generally are added dissolved in water, alkalis or organic acids, etc. If desired, they may be added by dissolving in organic solvents, which does not influence the bleach accelerating effect.

In case of incorporating the compounds of the present invention in the pre-bath for the bleaching solution or bleach-fix solution, baths having various compositions can be used as pre-baths. A pre-bath having the simplest composition is an aqueous solution in which the compounds of the present invention are merely dissolved. However, aqueous solutions containing acids such as acetic acid or boric acid, etc., alkalis such as sodium hydroxide, etc., or salts such as sodium sulfite, sodium acetate, sodium thiosulfate, sodium borate, sodium carbonate or sodium bicarbonate, etc., can be advantageously used, too. The pre-bath used may have a suitable pH, by which the effect of the present invention can be effectively demonstrated. However, since stains are sometimes generated with a pH which is too high, it is generally preferred that the pre-bath have a pH of 9 or less. The pre-bath may contain, if desired, agents for preventing precipitation using various kinds of chelating compounds, hardeners composed of various compounds including alum or aldehydes, pH buffer agents, fixing agents for halogen salts, antioxidants such as sulfites, hydroxylamine or hydrazine, etc., agents for preventing swelling such as sodium sulfate or magnesium sulfate, etc., and surface active agents, etc. For example, a water wash treatment, a stopping treatment or a stopping-fixing treatment, etc., may be interposed between the pre-bath and the bleaching bath or bleach-fixing bath. In such a case, the same bleach accelerating effect is obtained by adding the compounds of the present invention to the pre-bath. However, in case of using the compounds of the present invention in only the pre-bath, it is more preferred for the pre-bath to be used in the step just before the bleaching bath or bleach-fixing bath.

In the bleaching solution or the bleach-fixing solution used in the present invention, bleaching agents having a poor bleaching power are used. Examples include a ferric ion complex which is a complex of a ferric ion and a chelating agent such as aminopolycarboxylic acid, aminopolyphosphonic acid or a salt thereof, etc. Suitable salts of aminopolycarboxylic acids and salts of aminopolyphosphonic acids are alkali metal, ammonium of water-soluble amine salts of aminopolycarboxylic acids and aminopolyphosphonic acids. Examples of alkali metal salts are sodium, potassium and lithium, etc. salts. Suitable water-soluble amine salts are salts of alkylamines such as methylamine, diethylamine, triethylamine or butylamine, alicyclic amines such as cyclohexylamine, arylamines such as aniline or m-toluidine, and heterocyclic amines such as pyridine, morpholine or piperidine, etc.

Examples of these chelating agents such as aminopolycarobxylic acid, aminopolyphosphonic acid and salts thereof include the following compounds.
Ethylenediaminetetraacetic acid
Disodium ethylenediaminetetraacetate
Diammonium ethylenediaminetetraacetate
Tetra(trimethylammonium) ethylenediaminetetraacetate
Tetrapotassium ethylenediaminetetraacetate
Tetrasodium ethylenediaminetetraacetate
Trisodium ethylenediaminetetraacetate
Diethylenetriaminepentaacetic acid
Pentasodium diethylenetriaminepentaacetate
Ethylenediamine-N-($\beta$-oxyethyl)-N,N',N'-triacetic acid
Trisodium ethylenediamine-N-($\beta$-oxyethyl)-N,N',N'-triacetate
Triammonium ethylenediamine-N-($\beta$-oxyethyl)-N,N',N'-triacetate
Propylenediaminetetraacetic acid
Disodium propylenediaminetetraacetate
Nitrilotriacetic acid
Trisodium nitrilotriacetate
Cyclohexanediaminetetraacetic acid
Disodium cyclohexanediaminetetraacetate
Iminodiacetic acid
Dihydroxyethylglycine
Ethyl ether diaminetetraacetic acid
Glycol ether diaminetetraacetic acid
Ethylenediaminetetrapropionic acid
Phenylenediaminetetraacetic acid
1,3-Diaminopropanol-N,N,N',N'-tetramethylenephosphonic acid
Ethylenediamine-N,N,N',N'-tetramethylenephosphonic acid
1,3-Propylenediamine-N,N,N',N'-tetramethylenephosphonic acid
Of course, the chelating agents are not limited to these exemplified compounds.

The ferric ion complex salt may be used in the form of the complex salt or may be formed in solution by using ferric salts such as ferric sulfate, ferric chloride, ferric nitrate, ferric ammonium sulfate or ferric phosphate, etc., and chelating agents such as aminopolycarboxylic acids, aminopolyphosphonic acids or phosphonocarboxylic acids, etc. When used in the form of complex salt, one complex salt may be used or two or more complex salts may be used. On the other hand, in forming the complex salt in the solution by using ferric salts and chelating agents, one or two or more kinds of ferric salts may be used. Further, one or two or more kinds of chelating agents may be used. Further, in any case, the chelating agents may be used in an excess amount larger than that necessary to form ferric ion complex salts.

Further, the bleaching solution or the bleach-fixing solution containing the above described ferric ion complex may contain complex salts of metal ions other than iron, such as cobalt or copper, etc., or hydrogen peroxide.

Persulfates used in the bleaching solution and the bleach-fixing solution in the present invention include alkali metal persulfates such as potassium persulfate or sodium persulfate, and ammonium persulfate, etc. The bleaching accelerators of the present invention are effective, of course, for persulfates, but they show a particularly marked effect with ferric ion complex salts.

The bleaching solution in the present invention can contain, in addition to the bleaching agent such as ferric ion complex salt and the above described compounds, rehalogenating agents such as bromides, for example, potassium bromide, sodium bromide or ammonium bromide, or chlorides, for example, potassium chloride, sodium chloride or ammonium chloride, etc. In addition, it is possible to add known additives having a pH buffer ability used in conventional bleaching solutions, such as one or more inorganic acids, organic acids and salts thereof such as boric acid, borax, sodium metaborate, acetic acid, sodium acetate, sodium carbonate, potassium carbonate, phosphorous acid, phosphoric acid, sodium phosphate, citric acid sodium citrate and tartaric acid, etc.

In this case, the amount of the bleaching agent is about 0.1 to about 2 mols per liter of the bleaching solution, and the pH of the bleaching solution in use in preferably in the range of 3.0 to 8.0, particularly, 4.0 to 7.0, in case of ferric ion complex salts.

On the other hand, in using the composition of the present invention as a bleach-fixing agent, it is possible to use conventional fixing agents, namely, water-soluble silver halide solubilizing agents such as thiosulfates such as sodium thiosulfate, ammonium thiosulfate, ammonium sodium thiosulfate or potassium thiosulfate; thiocyanates such as sodium thiocyanate, ammonium thiocyanate or potassium thiocyanate; thioether compounds such as ethylenebisthioglycolic acid or 3,6-dithia-1,8-octanediol, and thioureas, etc., which may be used alone or as a mixture of two or more thereof. Further, it is possible to use specific bleach-fixing solutions consisting of a combination of a fixing agent and a large amount of a halogen compound such as potassium iodide, described in Japanese Patent Application (OPI) No. 155354/80.

In the bleach-fixing agent composition, it is preferred for the amount of the ferric ion complex salt to be in the range of about 0.1 to about 2 mols and the amount of the fixing agent to be in the range of about 0.2 to about 4 mols, per liter of the bleach-fixing solution.

The bleach-fixing agent may contain the above described additives to the bleaching solution and preservatives such as sulfites, for example, sodium sulfite, potassium sulfite and ammonium sulfite, and bisulfite addition products of hydroxylamine, hydrazine or aldehyde compounds, for example, acetaldehyde-sodium bisulfite, etc. Further, it is possible to use various fluorescent whitening agents, defoaming agents, surface active agents, organic solvents such as methanol, etc., and known compounds having a bleach-fixing accelerating capability, for example, polyamine compounds described in Japanese Patent Publication No. 8836/70, thiourea derivatives described in Japanese Patent Publication No. 8506/70, iodides described in German Pat. No. 1,127,715, polyethylene oxides described in German Pat. No. 966,410, nitrogen containing heterocyclic compounds described in German Pat. No. 1,290,812 and other thioureas, etc. Further, the pH of the bleach-fixing solution in use is preferred to be in the range of, generally, about 4.0 to about 9.0 and, particularly, 5.0 to 8.0.

The above described bleaching agent or the bleaching agent composition means both of the bleaching solution as a solution for use or a supplemental solution, and the bleach-fixing agent preparation for controlling the bleaching solution as a solution for use or a supplemental solution. Where the preparation is composed of two or more liquids, it is possible for the pH of the liquid containing ferric ion complex salt to be higher.

Aromatic primary amine type color developing agents which can be used in the color developing solution in the present invention are known agents used widely in various color photographic processes. These developing agents include aminophenol type derivatives and p-phenylenediamine type derivatives. These compounds are used generally in the form of the salt, for example, in the form of hydrochloride or sulfate salt, because the salt is more stable than the free compound. Further, these compounds are used in a concentration of about 0.1 g to about 30 g per liter of the color developing solution and, more preferably, in a concentration of about 1 g to about 15 g per liter of the color developing solution.

Examples of aminophenol type developing agents include o-aminophenol, p-aminophenol, 5-amino-2-oxytoluene, 2-amino-3-oxy-toluene and 2-oxy-3-amino-1,4-dimethyl-benzene, etc.

Particularly available aromatic primary amine type color developing agents are N,N-dialkyl-p-phenylenediamine compounds, the alkyl group and the phenyl group of which may be substituted or unsubstituted. Examples of particularly suitable compounds include N,N-diethyl-p-phenylenediamine hydrochloride, N-methyl-p-phenylenediamine hydrochloride, N,N-dimethyl-p-phenylenediamine hydrochloride, 2-amino-5-(N-ethyl-N-dodecylamino)toluene, N-ethyl-N-β-methanesulfonamidoethyl-3-methyl-4-aminoaniline sulfate, N-ethyl-N-β-hydroxyethylaminoaniline, 4-amino-3-methyl-N,N-diethylaniline, and 4-amino-N-(2-methoxyethyl)-N-ethyl-3-methylaniline-p-toluenesulfonate, etc.

The alkaline color developing solution used in the present invention can contain various components conventionally added to color developing solutions in addition to the above described aromatic primary amine type color developing agents. For example, alkali agents such as sodium hydroxide, sodium carbonate or potassium carbonate, alkali metal sulfites, alkali metal bisulfites, alkali metal thiocyanates, alkali metal halides, benzyl alcohol, water softeners and thickening agents, etc., can be used. The pH of this color developing solution is generally about 7 or more and more preferably in the range of about 9 to about 13.

The method of the present invention can be used for color reversal processing, too. As a black-white developing solution used in this case in the present invention, it is possible to use the conventionally known solution designated the first black-white developing solution for reversal processing of color photographic light-sensitive materials or the solution used for processing black-white light-sensitive materials. Further, it is possible to employ various known additives used generally for black-white developing solution.

Typical additives are developing agents such as 1-phenyl-3-pyrazolidone, Metol or hydroquinone, preservatives such as sulfites, accelerators composed of alkalis such as sodium hydroxide, sodium carbonate or potassium carbonate, etc., inorganic or organic restrainers such as potassium bromide, 2-methylbenzimidazole or methylbenzothiazole, etc., water softeners such as polyphosphates, and development restrainers composed of a very small amount of iodide or mercapto compounds.

The silver halide color photographic light-sensitive materials which can be processed in the presence of the compounds of the present invention according to the present invention are known color photographic light-sensitive materials. The present invention can be particularly advantageously used to process multilayer negative type color photographic light-sensitive materials containing couplers or color print photographic light-sensitive materials or color photographic light-sensitive materials for reversal color processing. Further, it is possible to process color X-ray photographic sensitive materials, monolayer specific color photographic light-sensitive materials, and color photographic light-sensitive materials which contain black-white developing agents such as 3-pyrazolidones described in U.S. Pat. Nos. 2,751,297 and 3,902,905, and Japanese patent applications (OPI) No. 64339/81, 85748/81 and 85749/81, and precursors of color developing agents described in U.S. Pat. Nos. 2,478,400, 3,342,597, 3,342,599, 3,719,492 and 4,214,047 and Japanese patent application (OPI) No. 135628/78 in the sensitive material. It is of course possible to use a developing solution containing couplers.

Any of silver bromide, silver iodobromide, silver iodochlorobromide, silver chlorobromide and silver chloride may be used as the silver halide in photographic emulsion layers in the color light-sensitive materials used in the present invention. The average particle size of the silver halide grains in the photographic emulsions (which is represented as the average based on projected areas, wherein the particle size means the diameter of grains in case of spherical or nearly spherical grains and the side line length in case of cubic grains) is not restricted, but it is preferred to be about 3.0μ or less. The distribution of particle size may be either narrow or broad.

Photographic emulsions which can be processed in the present invention can be prepared by processes described in P. Glafkides, *Chimie et Physique Photographique*, Paul Montel Co. (1967), G. F. Duffin, *Photographic Emulsion Chemistry*, The Focal Press (1966), and V. L. Zelikman, et al., *Making and Coating Photographic Emulsion*, The Focal Press (1964), etc.

The formation of silver halide grains or physical aging may be carried out in the presence of cadmium salts, zinc salts, lead salts, thallium salts, iridium salts or complex salts thereof, rhodium salts or complex salts thereof, or iron salts or complex salts thereof.

In the present invention, it is possible to use negative type emulsions forming surface latent images and direct reversal emulsions. Inner latent image type emulsions and previously fogged direct reversal emulsions are examples of the latter emulsions.

Although silver halide emulsions can be used without carrying out chemical sensitization, as the socalled primitive emulsions, they are generally subjected to chemical sensitization. In order to carry out chemical sensitization, it is possible to use processes described in the above described books written by Glafkides, or Zelikman, et al., and H. Frieser Ed., *Die Grundlagen der Photographischen Prozesse mit Silberhalogeniden*, Akademische Verlagsgesellschaft (1968).

Namely, it is possible to use a sulfur sensitization process using sulfur containing compounds or active gelatin capable of reacting with silver ion, a reduction sensitization process using reducing substances, and a noble metal sensitization process using gold or other noble metal compounds, etc., which may be used alone or as a combination thereof. As sulfur sensitizers, it is possible to use thiosulfates, thioureas, thiazoles, rhodanines and other compounds.

As reduction sensitizers, it is possible to use stannous salts, amines, hydrazine derivatives, formamidine sulfinic acid and silane compounds, etc.

In order to carry out noble metal sensitization, it is possible to use gold complex salts and complex salts of metal of group VIII in the Periodic Table such as platinum, iridium or palladium, etc.

Photographic emulsions may be spectrally sensitized with methine dyes and other dyes. Examples of dyes which can be used include cyanine dyes, merocyanine dyes, complex cyanine dyes, complex merocyanine dyes, holopolar cyanine dyes, hemicyanine dyes, styryl dyes and hemioxonol dyes. Particularly suitable dyes are cyanine dyes, merocyanine dyes and complex merocyanine dyes.

In addition to the above described light-sensitive silver halide emulsion layers, layers of substantially nonsensitive fine grain silver halide emulsions may be provided in order to improve granularity or sharpness or for other purposes. A substantially nonsensitive fine grain emulsion layer can be provided on the light-sensitive silver halide emulsion layer or between the light-sensitive silver halide emulsion layer and a colloidal silver layer (a yellow filter layer or an antihalation layer).

The light-sensitive materials used in the present invention may contain, for example, polyalkylene oxides and derivatives thereof such as ethers, esters or amines, etc., thioether compounds, thiomorpholines, quaternary ammonium salt compounds, urethane derivatives, urea derivatives, imidazole derivatives and 3-pyrazolidones, etc., for the purpose of increasing sensitivity, increasing contrast or accelerating development.

Gelatin is advantageously used as a binder for the photographic emulsion layer and other layers, but other hydrophilic colloids can be used, too.

The light-sensitive materials used in the present invention can contain various compounds as antifogging agents or stabilizers. Namely, it is possible to employ various compounds known as antifogging agents or stabilizers, such as azoles, for example, benzothiazolium salt, nitroimidazoles, and benzimidazoles (particularly, nitro- or halogen-substituted derivatives); heterocyclic mercapto compounds, for example, mercaptothiazoles, mercaptobenzothiazoles, mercaptothiadiazoles, mercaptotetrazoles (particularly, 1-phenyl-5-mercaptotetrazole), and mercaptopyrimidines; the above described heterocyclic mercapto compounds which have water solubilizing groups such as carboxyl groups or sulfonic acid groups, etc.; thioketo compounds, for example, oxazolinethione; azaindenes, for example, tetraazaindenes (particularly, 4-hydroxy-substituted (1,3,3a,7-tetraazaindenes); benzenethiosulfonic acids; or benzenesulfinic acid; etc.

The photographic emulsion layers and other layers in the photographic light-sensitive materials used in the present invention may contain inorganic or organic hardeners. For example, it is possible to use chromium salts (chromium alum and chromium acetate, etc.), aldehydes (formaldehyde, glyoxal and glutaraldehyde, etc.), N-methylol compounds (dimethylolurea and methylol dimethylhydantoin, etc.), dioxane derivatives (2,3-dihydroxydioxane, etc.), active vinyl compounds (1,3,5-triacryloylhexahydro-s-triazine and 1,3-vinylsulfonyl-2-propanol, etc.), active halogen compounds (2,4-dichloro-6-hydroxy-s-triazine, etc.) and mucohalogenic acids (mucochloric acid and mucophenoxychloric acid, etc.), etc., which maybe used alone or as a combination thereof.

The photographic emulsion layers and other layers in the light-sensitive materials used in the present invention may contain various surface active agents for various purposes, for example, as coating aids, for prevention of charging, for improvement of lubricating property, for emulsification or dispersion, for prevention of adhesion and for improvement of photographic properties (for example, acceleration of development, hard toning or sensitization), etc.

The photographic emulsion layers in the light-sensitive materials used in the present invention may contain color forming couplers, namely, compounds which form a color by oxidative coupling with an aromatic primary amine developing agent (for example, phenylenediamine derivatives or aminophenol derivatives, etc.) in the color development processing. For example, as magenta couplers, there are 5-pyrazolone couplers, pyrazolobenzimidazole couplers, cyanoacetylcoumarone couplers and ring-opened acylacetonitrile couplers, etc. As yellow couplers, there are acylacetamide couplers (for example, benzoylacetanilides and pivaloylacetanilides), etc. As cyan couplers, there are naphthol couplers and phenol couplers, etc. It is preferred for these couplers to be nondiffusible couplers having hydrophobic groups called ballast groups in the molecule. The couplers may be 4-equivalent couplers and 2-equivalent couplers to silver ion. Further, they may be colored couplers having a color correction effect or couplers which release a development inhibitor by development (the so-called DIR couplers). Further, they may include noncoloring DIR coupling compounds which form a colorless product by a coupling reaction and release a development inhibitor and DIR redox compounds other than DIR couplers.

Examples of magenta couplers include those described in U.S. Pat. Nos. 2,600,788, 2,983,608, 3,062,653, 3,127,269, 3,311,476, 3,419,391, 3,519,429, 3,558,319, 3,582,322, 3,615,506, 3,834,908 and 3,891,445, West German Pat. No. 1,810,464, West German patent applications (OLS) Nos. 2,408,665, 2,417,945, 2,418,959 and 2,424,467, Japanese Patent Publication No. 6031/65, and Japanese patent application (OPI) Nos. 20826/76, 13041/75, 58922/77, 129538/74, 74027/74, 159336/75, 42121/77, 74028/74, 60233/75, 26541/76 and 55122/78, etc.

Examples of yellow couplers include those described in U.S. Pat. Nos. 2,875,057, 3,265,506, 3,408,194, 3,551,155, 3,582,322, 3,725,072 and 3,891,445, West German Pat. No. 1,547,868, West German patent application (OLS) Nos. 2,219,917, 2,261,361 and 2,414,006, British Patent No. 1,425,020, Japanese patent publication No. 10783/76, and Japanese patent application (OPI) Nos. 26133/72, 73147/73, 102636/76, 6341/75, 123342/75, 130442/75, 21827/76, 87650/75, 82424/77 and 115219/77, etc.

Examples of cyan couplers include those described in U.S. Pat. Nos. 2,369,929, 2,434,272, 2,474,293, 2,521,908, 2,895,826, 3,034,892, 3,311,476, 3,458,315, 3,476,563, 3,583,971, 3,591,383, 3,767,411 and 4,004,929, West German patent application (OLS) Nos. 2,414,830 and 2,454,329, Japanese patent application (OPI) Nos. 59838/73, 26034/76, 5055/73, 146828/76, 69624/77 and 90932/77. Further, couplers which have good fastness to heat and light and cause less deterioration of dye density even if processed with a bleaching agent having a poor oxidizing power are the couplers described in U.S. Pat. Nos. 4,124,396, 4,327,173, 4,333,999 and 4,334,011, and Japanese patent application (OPI) Nos. 155538/72 and 204545/72.

Examples of colored couplers include those described in U.S. Pat. Nos. 3,476,560, 2,521,908 and 3,034,892, Japanese patent publication Nos. 2016/69, 22335/63, 11304/67 and 32461/69, Japanese patent application (OPI) Nos. 26034/76 and 42121/77, and West German patent application (OLS) No. 2,418,959.

Examples of DIR couplers include o-aminoazo type DIR couplers described in U.S. Pat. No. 3,148,062, thioether type DIR couplers described in U.S. Pat. No. 3,227,554, 2-benzotriazolyl type DIR couplers described in U.S. Pat. No. 3,617,291, 1-benzotriazolyl type DIR couplers described in West German patent application (OLS) No. 2,414,006 and Japanese patent application (OPI) Nos. 82424/77 and 117627/77, nitrogen containing heterocycle substituted acetic acid ester type DIR couplers described in Japanese patent application (OPI) Nos. 30591/75 and 82423/77, 2-equivalent DIR cyan couplers described in West German patent application (OLS) No. 2,527,652 and Japanese patent application (OPI) Nos. 90932/77 and 146828/76, and malondiamide type DIR couplers described in Japanese patent application (OPI) No. 69624/77.

Examples of noncoloring DIR coupling compounds include thioether type cyclic noncoloring DIR compounds described in British Pat. No. 1,423,588, West German patent application (OLS) Nos. 2,405,442, 2,523,705, 2,529,350 and 2,448,063 and U.S. Pat. No. 3,938,996, thioether type chain noncoloring DIR compounds described in U.S. Pat. Nos. 3,632,345 and 3,928,041, benzotriazolyl type noncoloring DIR compounds described in Japanese patent application (OPI) Nos. 147716/75, 105819/76 and 67628/77, and picolinium type DIR coupling compounds described in Japanese patent application (OPI) No. 72433/76.

Examples of DIR redox compounds include DIR hydroquinones described in U.S. Pat. No. 3,639,417, West German patent application (OLS) No. 2,460,202 and U.S. Pat. No. 3,297,445 and DIR redox type couplers described in Japanese patent application (OPI) No. 57828/77, etc.

The light-sensitive materials used in the present invention can contain developing agents. As the developing agents, those described in *Research Disclosure*, Vol. 176, p. 29 "Developing Agents" can be used.

In the light-sensitive materials used in the present invention, the photographic emulsion layers and other layers may contain dyes as filter dyes or for the purpose of preventing irradiation and others. As such dyes, those described in *Research Disclosure*, Vol. 176, pp. 25–26 "Absorbing and Filter Dyes" are used.

The light-sensitive materials used in the present invention may contain antistatic agents, plasticizers, matting agents, lubricants, ultraviolet light absorbing agents, fluorescent whitening agents and air-antifogging agents, etc.

The silver halide emulsion layers and/or other layers are applied to a support. Coating can be carried out by processes described in *Research Disclosure*, Vol. 176, pp. 27–28 "Coating Procedures".

Since the compounds of the present invention have a very large bleach accelerating effect, desilvering can be sufficiently carried out in a short processing time even if a bleaching agent having a poor bleaching power is used. Further, the compounds of the present invention do not adversely influence color development and photographic properties such as sensitivity and stain characteristic, etc. Further, since the compounds of the present invention are stable for a long period of time in the bath, it is possible to reduce concerns on control of the bath.

The present invention is illustrated in greater detail by reference to the following examples.

EXAMPLE 1

To a triacetyl cellulose support having a subbing layer, emulsion layers and auxiliary layers were applied in the following order to produce a sample.

First Layer: Low Speed Red-Sensitive Emulsion Layer 500 g of an emulsion which was prepared by dissolving 100 g of cyan coupler: 2-(heptafluorobutyramido)-5-[2'-(2'',4''-di-t-amylphenoxy)-butyramido]phenol, in a mixture of 100 cc of tricresyl phosphate and 100 cc of ethyl acetate and stirring at a high rate together with 1 kg of a 10% aqueous solution of gelatin, was blended with 1 kg of a red-sensitive low speed silver iodobromide emulsion (containing 70 g of silver and 60 g of gelatin and having an iodine content of 3% by mol), and the mixture was applied in a dry film thickness of 2.0 $\mu$(silver amount: 0.5 g/m$^2$).

Second Layer: High Speed Red-Sensitive Emulsion Layer 1 kg of an emulsion which was prepared by dissolving 100 g of cyan coupler: 2-(heptafluorobutyramido)-5-[2'-(2'',4''-di-t-amylphenoxy)-butyramido]phenol, in a mixture of 100 cc of tricresyl phosphate and 100 cc of ethyl acetate, and stirring at a high rate together with 1 kg of a 10% aqueous solution of gelatin, was blended with 1 kg of a red-sensitive high speed silver iodobromide emulsion (containing 70 g of silver and 60 g of gelatin and having an iodine content of 3% by mol), and the mixture was applied in a dry film thickness of 2.0$\mu$ (silver amount: 0.8 g/m$^2$).

Third Layer: Intermediate Layer 1 kg of an emulsion which was prepared by dissolving 60 g of 2,5-di-t-octylhydroquinone in a mixture of 100 cc of dibutyl phthalate and 100 cc of ethyl acetate and stirring at a high rate together with 1 kg of a 10% aqueous solution of gelatin, was blended with 1 kg of a 10% solution of gelatin. The mixture was applied in a dry film thickness of 1.0$\mu$.

Fourth Layer: Low Speed Green-Sensitive Emulsion Layer 500 g of an emulsion prepared in the same manner as the emulsion for the First Layer, except that a magenta coupler: 1-(2,4,6-trichlorophenyl)-3-[3-(2,4-di-t-amyl-phenoxyacetamido)benzamido]-5-pyrazolone, was used instead of the cyan coupler, was blended with 1 kg of a green-sensitive low speed silver iodobromide emulsion (containing 70 g of silver and 60 g of gelatin and having an iodine content of 2.5% by mol), and the mixture was applied in a dry film thickness of 2.0$\mu$ (silver amount: 0.7 g/m$^2$).

Fifth Layer: High Speed Green-Sensitive Emulsion Layer 1 kg of an emulsion prepared in the same manner as the emulsion for the First Layer, except that 1-(2,4,6-trichlorophenyl)-3-[3-(2,4-di-t-amylphenoxyacetamido)-benzamido]-5-pyrazolone was used as a magenta coupler instead of the cyan coupler, was blended with 1 kg of a green-sensitive high speed silver iodobromide emulsion (containing 70 g of silver and 60 g of gelatin and having an iodine content of 2.5% by mol), and the resulting mixture was applied in a dry film thickness of 2.0μ (silver amount: 0.7 g/m$^2$).

Sixth Layer: Intermediate Layer 1 kg of an emulsion used in the Third Layer was blended with 1 kg of a 10% solution of gelatin, and the mixture was applied in a dry film thickness of 1.0μ.

Seventh Layer: Yellow Filter Layer P An emulsion containing yellow colloidal silver was applied in a dry film thickness of 1.0μ.

Eighth Layer: Low Speed Blue-Sensitive Emulsion Layer 1 kg of an emulsion prepared in the same manner as the emulsion for the First Layer, except that the yellow coupler: α-(pivaloyl)-α-(1-benzyl-5-ethoxy-3-hydantoinyl)-2-chloro-5-dodecyloxycarbonylacetanilide, was used instead of the cyan coupler, was blended with 1 kg of a blue-sensitive low speed silver iodobromide emulsion (containing 70 g of silver and 60 g of gelatin and having an iodine content of 2.5% by mol), and the resulting mixture was applied in a dry film thickness of 2.0μ (silver amount: 0.6 g/m$^2$).

Ninth Layer: High Speed Blue-Sensitive Emulsion Layer 1 kg of an emulsion prepared in the same manner as the emulsion for the First Layer except that the yellow coupler: α-(pivaloyl)-α-(1-benzyl-5-ethoxy-3-hydantoinyl)-2-chloro-5-dodecyloxycarbonylacetanilide, was used instead of the cyan coupler, was blended with 1 kg of a blue-sensitive high speed silver iodobromide emulsion (containing 70 g of silver and 60 g of gelatin and having an iodine content of 2.5% by mol), and the resulting mixture was applied in a dry film thickness of 2.0μ (silver amount: 1.0 g/m$^2$).

Tenth Layer: The Second Protective Layer 1 kg of an emulsion used in the Third Layer was blended with 1 kg of a 10% aqueous solution of gelatin, and the resulting mixture was applied in a dry film thickness of 2.0μ.

Eleventh Layer: The First Protective Layer

A 10% wt. aqueous solution of gelatin containing a fine grain emulsion which was not chemically sensitized (particle size: 0.15μ, 1 mol% silver iodobromide emulsion) was applied in a silver amount of 0.3 g/m$^2$ and a dry film thickness of 1.0μ.

The resulting color reversal film was exposed to light using a tungsten lamp at an appropriate exposure adjusted to a color temperature of 4,800° K. using a filter, and it was subjected to development processing using various kinds of bleaching solutions to which compounds of the present invention were added as shown in Table 1 below, according to the following development processing steps.

| First Development Bath | 6 minutes | 38° C. |
|---|---|---|
| Water Wash | 2 minutes | " |
| Reversal Bath | 2 minutes | " |
| Color Development Bath | 6 minutes | " |
| Controlling Bath | 2 minutes | " |
| Bleaching Bath | 5 minutes | " |
| Fixing Bath | 4 minutes | " |
| Water Wash | 4 minutes | " |
| Stabilizing Bath | 1 minute | Room Temperature |

The compositions of the processing solutions used were as follows.

| First Development Bath | |
|---|---|
| Water | 700 ml |
| Sodium Tetrapolyphosphate | 2 g |
| Sodium Sulfite | 20 g |
| Hydroquinone Monosulfonate | 30 g |
| Sodium Carbonate (monohydrate) | 30 g |
| 1-Phenyl-4-methyl-4-hydroxymethyl-3-pyrazolidone | 2 g |
| Potassium Bromide | 2.5 g |
| Potassium Thiocyanate | 1.2 g |
| Potassium Iodide (0.1% wt. solution) | 2 ml |
| Water to make | 1,000 ml |
| | pH: 10.1 |
| Reversal Bath: | |
| Water | 700 ml |
| Nitrilo-N,N,N—trimethylenephosphonic Acid 6 Na Salt | 3 g |
| Stannous Chloride (dihydrate) | 1 g |
| p-Aminophenol | 0.1 g |
| Sodium Hydroxide | 8 g |
| Glacial Acetic Acid | 15 ml |
| Water to make | 1,000 ml |
| Color Development Bath: | |
| Water | 700 ml |
| Sodium Tetrapolyphosphate | 2 g |
| Sodium Sulfite | 7 g |
| Sodium Tertiary Phosphate (dodecahydrate) | 36 g |
| Potassium Bromide | 1 g |
| Potassium Iodide (0.1% wt. aq. soln.) | 90 ml |
| Sodium Hydroxide | 3 g |
| Citrazinic Acid | 1.5 g |
| N—Ethyl-N—(β-methanesulfonamidoethyl)-3-methyl-4-aminoaniline Sulfate | 11 g |
| Ethylenediamine | 3 g |
| Water to make | 1,000 ml |
| Controlling Bath: | |
| Water | 700 ml |
| Sodium Sulfite | 12 g |
| Sodium Ethylenediaminetetraacetate (dihydrate) | 8 g |
| Glacial Acetic Acid | 3 ml |
| Water to make | 1,000 ml |
| Bleaching Bath: | |
| Water | 800 ml |
| Sodium Ethylenediaminetetraacetate (dihydrate) | 2.0 g |
| Ethylenediaminetetraacetate iron (III) Ammonium Salt (dihydrate) | 120.0 g |
| Potassium Bromide | 100.0 g |
| Water to make | 1,000 ml |
| Fixing Bath: | |
| Water | 800 ml |
| Ammonium Thiosulfate | 80.0 g |
| Sodium Sulfite | 5.0 g |
| Sodium Bisulfite | 5.0 g |
| Water to make | 1,000 ml |
| Stabilizing Bath: | |
| Water | 800 ml |
| Formaldehyde (37% wt. aq. soln.) | 5.0 ml |
| Fuji Driwel | 5.0 ml |
| Water to make | 1,000 ml |

The amount of silver remaining in the maximum density part in each film sample which was subjected to the above described development processing was measured by X-ray fluorometry. Results obtained are as follows.

TABLE 1

| Sample | Bleaching Accelerator | Amount Added to Bleaching Bath | Residual Silver Amount (μg/cm²) |
|---|---|---|---|
| 1 | None | — | 15 |
| 2 | Compound 1 | $5 \times 10^{-3}$ mol/l | 4.2 |
| 3 | Compound 2 | " | 5.5 |
| 4 | Compound 3 | " | 4.3 |
| 5 | Compound 4 | " | 3.1 |
| 6 | Compound 7 | " | 3.3 |
| 7 | Compound 10 | " | 2.0 |

In films processed with the bleaching baths containing the compounds of the present invention, the residual silver left in the film without desilvering was removed to an insignificant degree and, thus, clear dye images were obtained.

When the compounds of the present invention were used, it became possible to carry out rapid development processing with low pollution.

EXAMPLE 2

Reversal processing was carried out in the same manner as described in Example 1, except that compounds of the present invention were added to the controlling bath instead of the bleaching bath in the processing steps. The amount of silver remaining in the film was determined by the same method as in Example 1. The results obtained are shown in Table 2 below.

TABLE 2

| Sample | Bleaching Accelerator | Amount Added to Controlling Bath | Residual Silver Amount (μg/cm²) |
|---|---|---|---|
| 8 | None | — | 17 |
| 9 | Compound 1 | $1 \times 10^{-2}$ mol/l | 4.7 |
| 10 | Compound 7 | " | 3.5 |
| 11 | Compound 3 | " | 4.3 |
| 12 | Compound 10 | " | 2.6 |
| 13 | Compound 12 | " | 3.0 |

It can be seen that desilvering is accelerated similarly to the case of adding the compounds of the present invention to the bleaching bath, if they are added to the controlling bath.

EXAMPLE 3

Reversal processing was carried out in the same manner as described in Example 1, except that the controlling bath in the processing steps was removed and a bleach-fixing solution having the following composition, to which Compounds 5, 3 and 10 of the present invention were added, respectively, was used instead of the bleaching solution and the fixing solution (bleach-fixing time was 6 minutes). The amount of silver remaining in the film was determined in the same manner as in Example 1. The results are shown in Table 3 below.

| Bleach-Fixing Bath: | |
|---|---|
| Ethylenediaminetetraacetic Acid Ferric Ammonium Salt Dihydrate | 120.0 g |
| Disodium Ethylenediaminetetraacetate | 5.0 g |
| Ammonium Thiosulfate (70% wt. aq. soln.) | 170.0 ml |
| Sodium Sulfite | 10.0 g |
| Water to make | 1,000 ml |
| | pH: 6.5 |

TABLE 3

| Sample | Bleaching Accelerator | Amount Added to Bleach-Fixing Solution | Residual Silver Amount (μg/cm²) |
|---|---|---|---|
| 14 | None | — | 110 |
| 15 | Compound 3 | $5 \times 10^{-3}$ mol/l | 3.6 |
| 16 | Compound 5 | " | 5.9 |
| 17 | Compound 10 | " | 2.3 |

It can be seen that desilvering is accelerated similarly to the case of adding the compounds of the present invention to the bleaching bath, if they are added to the bleach-fixing solution.

EXAMPLE 4

A multilayer color light-sensitive material was produced by applying layers having the following compositions to a polyethylene terephthalate film support.

First Layer: Antihalation Layer
  Gelatin layer containing black colloidal silver
Second Layer: Intermediate Layer
  Gelatin layer containing an emulsified dispersion of 2,5-di-t-octylhydroquinone
Third Layer: Low Speed Red-Sensitive Emulsion Layer
  Silver iodobromide emulsion (silver iodide: 5% by mol)—Silver amount: 1.6 g/m²
  Sensitizing Dye I—$6 \times 10^{-5}$ mol per mol of silver
  Sensitizing Dye II—$1.5 \times 10^{-5}$ mol per mol of silver
  Coupler EX-1—0.04 mol per mol of silver
  Coupler EX-5—0.003 mol per mol of silver
  Coupler EX-6—0.0006 mol per mol of silver
Fourth Layer: High Speed Red-Sensitive Emulsion Layer
  Silver iodobromide emulsion (silver iodide: 10% by mol)—Silver amount: 1.4 g/m²
  Sensitizing Dye I—$3 \times 10^{-5}$ mol per mol of silver
  Sensitizing Dye II—$1.2 \times 10^{-5}$ mol per mol of silver
  Coupler EX-2—0.02 mol per mol of silver
  Coupler EX-5—0.0016 mol per mol of silver
Fifth Layer: Intermediate Layer
  The same as the Second Layer
Sixth Layer: Low Speed Green-Sensitive Emulsion Layer
  Monodispersed silver iodobromide emulsion (silver iodide: 4% by mol)—Silver amount: 1.2 g/m²
  Sensitizing Dye III—$3 \times 10^{-5}$ mol per mol of silver
  Sensitizing Dye IV—$1 \times 10^{-5}$ mol per mol of silver
  Coupler EX-4—0.05 mol per mol of silver
  Coupler EX-8—0.008 mol per mol of silver
  Coupler EX-6—0.0015 mol per mol of silver
Seventh Layer: High Speed Green-Sensitive Emulsion Layer
  Silver iodobromide emulsion (silver iodide: 10% by mol)—Silver amount: 1.3 g/m²
  Sensitizing Dye III—$2.5 \times 10^{-5}$ mol per mol of silver
  Sensitizing Dye IV—$0.8 \times 10^{-5}$ mol per mol of silver
  Coupler EX-3—0.017 mol per mol of silver
  Coupler EX-8—0.003 mol per mol of silver
  Coupler EX-10—0.003 mol per mol of silver
Eighth Layer: Yellow Filter Layer
  Gelatin layer containing yellow colloidal silver and an emulsified dispersions of 2,5-di-t-octylhydroquinone
Ninth Layer: Low Speed Blue-Sensitive Emulsion Layer
  Silver iodobromide emulsion (silver iodide: 6% by mol)—Silver amount: 0.7 g/m²
  Coupler EX-9—0.25 mol per mol of silver Coupler EX-6—0.015 mol per mol of silver Tenth Layer: High Speed Blue-Sensitive Emulsion Layer Silver iodobromide emulsion (silver iodide: 6% by mol)—Silver amount: 0.6 g/m²

Coupler EX-9—0.06 mol per mol of silver

Eleventh Layer: The First Protective Layer

Silver iodobromide (silver iodide: 1% by mol, average particle size: 0.07μ)—Silver amount: 0.5 g/m²

Gelatin layer containing an emulsified dispersion of the ultraviolet light absorbing agent UV-1

Twelfth Layer: The Second Protective Layer

Gelatin layer containing trimethylmethanoacrylate particles (diameter: about 1.5μ)

To each layer, Gelatin Hardener H-1 and surface active agents were added in addition to the above described composition.

The sample produced as described above is designated Sample 101.

The compounds used for Sample 101 are as follows.

Sensitizing Dye I: Anhydro-5,5'-dichloro-3,3'-di(γ-sulfopropyl)-9-ethyl-thiacarbocyanine hydroxide pyridinium salt Sensitizing Dye II: Anhydro-9-ethyl-3,3'-di(γ-sulfopropyl)-4,5,4',5'-dibenzothiacarbocyanine hydroxide triethylamine salt Sensitizing Dye III: Anhydro-9-ethyl-5,5'-dichloro3,3'-di(γ-sulfopropyl)oxacarbocyanine sodium salt Sensitizing Dye IV: Anhydro-5,6,5',6'-tetrachloro-1,1'-diethyl-3,3'-di{β-[β-(γ-sulfopropyl)ethoxy]-ethyl}imidazolocarbocyanine hydroxide sodium salt

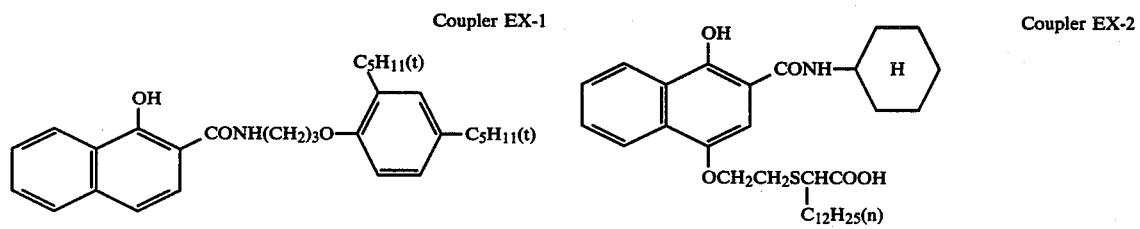

Coupler EX-1

Coupler EX-2

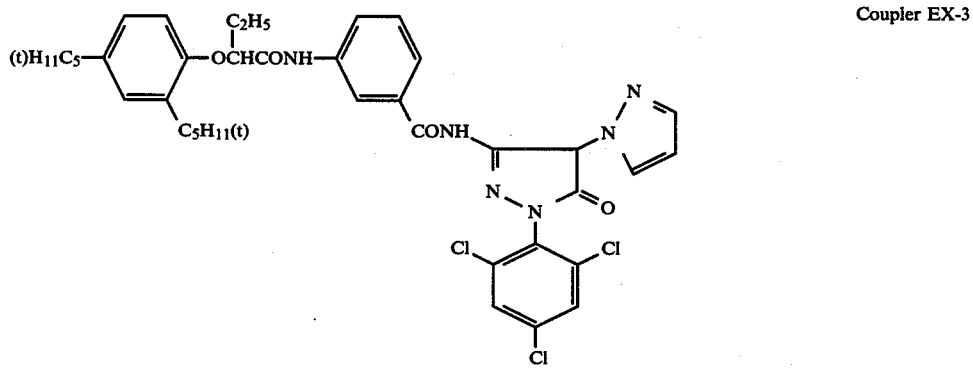

Coupler EX-3

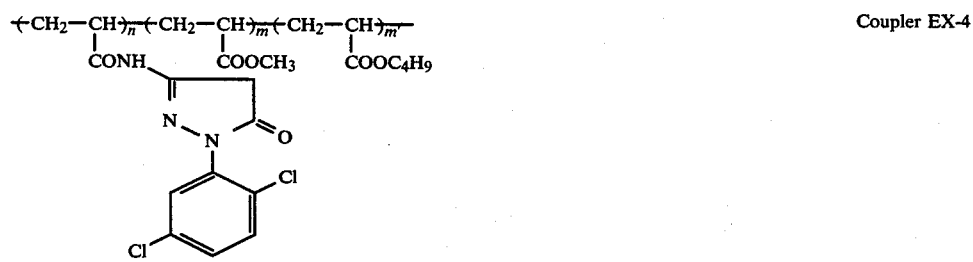

Coupler EX-4 n/m + m' = 1, m/m' = 1 (ratio by weight)
molecular weight: about 40,000

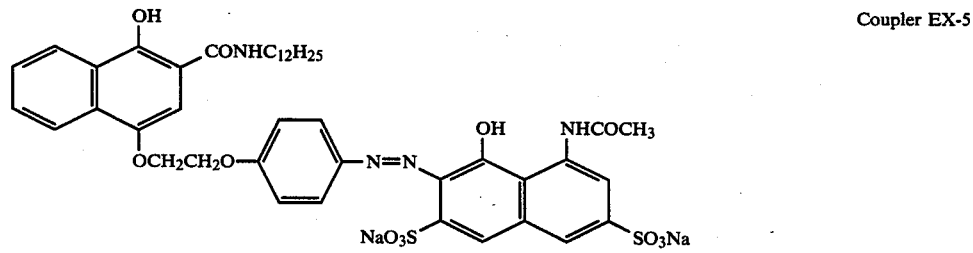

Coupler EX-5

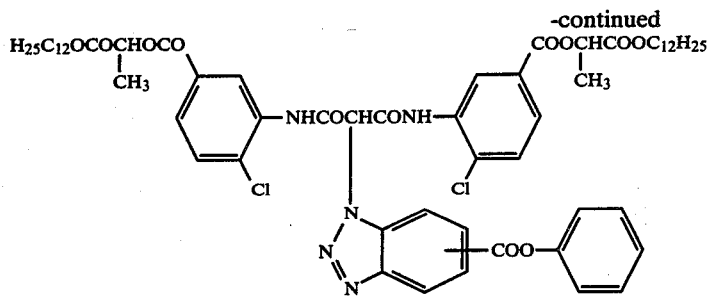

Coupler EX-6

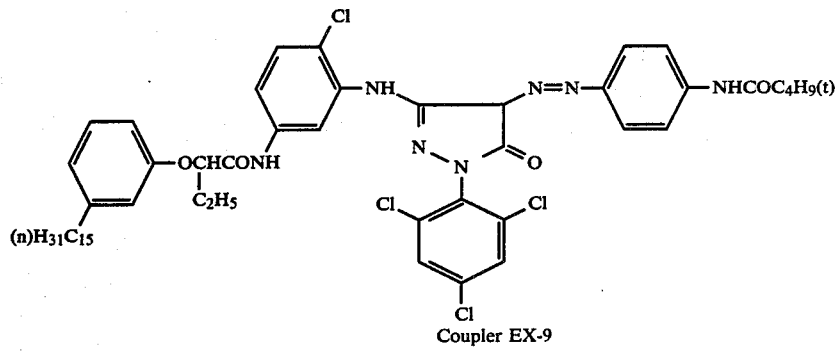

Coupler EX-8

Coupler EX-9

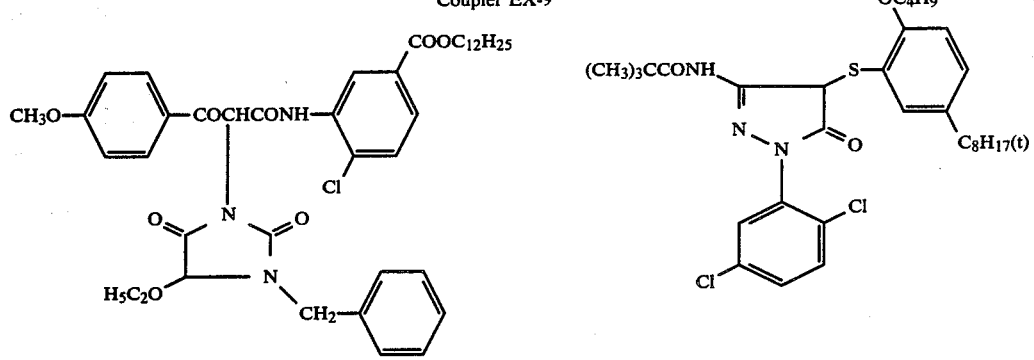

Coupler EX-10

H$_2$CHCSO$_2$CH$_2$CONH(CH$_2$)$_2$NHCOCH$_2$SO$_2$CH=CH$_2$  Gelatin Hardener H-1

Ultraviolet Light Absorbent UV-1

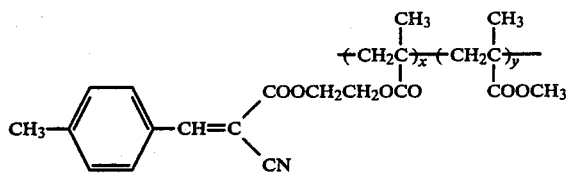

x/y = 7/3 (ratio by weight)

After this photographic element was subjected to exposure at 25 CMS using a tungsten lamp the color temperature of which was controlled to 4,800° K. using a filter, it was subjected to development processing at 38° C. according to the following processing steps.

| Color Development | 3 minutes and 15 seconds |
| --- | --- |
| Bleach | 4 minutes and 20 seconds |
| Fix | 4 minutes and 20 seconds |
| Water Wash | 3 minutes and 15 seconds |
| Stabilization | 30 seconds |

The compositions of the processing solutions used in each step were as follows.

| Color Developing Solution: | |
| --- | --- |
| Trisodium Nitrilotriacetate | 1.9 g |
| Sodium Sulfite | 4.0 g |
| Potassium Carbonate | 30.0 g |
| Potassium Bromide | 1.4 g |
| Potassium Iodide | 1.3 mg |
| Hydroxylamine Sulfate | 2.4 g |
| 4-(N—Ethyl-N—β-hydroxyethylamino)-2-methylaniline Sulfate | 4.5 g |
| Water to make | 1.0 l |
| | pH: 10.0 |
| Bleaching Solution: | |
| Ethylenediaminetetraacetic Acid Ferric Ammonium Salt | 80.0 g |
| Disodium Ethylenediaminetetraacetate | 8.0 g |
| Ammonium Bromide | 120.0 g |
| Compound of the Present Invention | (amount described |

-continued

| (described in Table 4) | in Table 4) |
|---|---|
| Water to make | 1.0 l |
| | pH: 6.0 |
| Fixing Solution: | |
| Sodium Tetrapolyphosphate | 2.0 g |
| Sodium Sulfite | 4.0 g |
| Ammonium Thiosulfate (70% wt. aq. soln.) | 175.0 ml |
| Sodium Bisulfite | 4.6 g |
| Water to make | 1.0 ml |
| | pH: 6.6 |
| Stabilizing Solution: | |
| Formaldehyde (40% wt. aq. soln.) | 8.0 ml |
| Water to make | 1.0 l |

Further, development processing was carried out as described above using a bleaching solution having the same composition as described above, except that the compound of the present invention was not employed.

The amount of silver left in the maximum density parts of each film sample which was subjected to the above described development processing was measured by X-ray fluorometry. Results obtained are shown in Table 4 below.

TABLE 4

| Sample | Bleaching Accelerator | Amount Added to Bleaching Bath | Residual Silver Amount ($\mu g/cm^2$) |
|---|---|---|---|
| 18 | None | $5 \times 10^{-3}$ mol/l | 11.5 |
| 19 | Compound 4 | " | 2.8 |
| 20 | Compound 10 | " | 1.7 |
| 21 | Compound 13 | " | 2.0 |

It can be seen from the results in Table 4 that desilvering is remarkably accelerated by using compounds of the present invention (Samples 19 to 21) as compared with the comparative example (Sample 18) which does not contain the compound of the present invention.

EXAMPLE 5

The same processing as described in Example 4 was carried out, except that a bleach-fixing solution having the following composition to which the compound of the present invention or a comparative compound (described in Table 5) was added was used in the processing steps in Example 4 instead of the bleaching solution and the fixing solution (bleach-fixing time was 3 minutes and 15 seconds). The amount of silver left in the film was determined using the same method as described in Example 4. After the bleach-fixing solutions were allowed to stand for 2 days in a constant temperature bath at 40° C., bleaching ability of them was examined. Results obtained are shown in Table 5 below.

| Bleach-Fixing Solution: | |
|---|---|
| Ethylenediaminetetraacetic Acid Ferric Ammonium Salt Dihydrate | 100.0 g |
| Disodium Ethylenediaminetetraacetate Dihydrate | 5.0 g |
| Sodium Sulfite | 10.0 g |
| Ammonium Thiosulfate (70% wt. aq. soln.) | 170.0 ml |
| Water to make | 1.0 l |
| | pH: 6.9 |

TABLE 5

| Sample | Bleaching Accelerator | Amount Added to Bleach-Fixing Solution (mol/l) | Residual Silver Amount ($\mu g/cm^2$) | Residual Silver Amount after Standing at 40° C. for 2 Days ($\mu g/cm^2$) |
|---|---|---|---|---|
| 22 | None | — | 55.0 | 57.2 |
| 23 | Compound 4 | $5 \times 10^{-3}$ | 2.2 | 3.0 |
| 24 | Compound 10 | " | 1.4 | 2.1 |
| 25 | Compound 12 | " | 1.2 | 1.9 |
| 26 | 4-Carobxy-thiazolidine* | " | 12.0 | 56.8 |

*Compound described in Japanese Patent Publication 9854/78

It can be seen from the results in Table 5 that desilvering is markedly accelerated and bleach-fixing of high-speed negative sensitive materials can be rapidly carried out by using compounds of the present invention (Samples 23 to 25) as compared with Sample 22 which does not contain the compound of the present invention and Sample 26 containing the known compound which is beyond the scope of the present invention. Further, it can be seen that when the bleach-fixing solutions are allowed to stand for 2 days in a constant temperature bath at 40° C., Samples 23 to 25 using the compounds of the present invention do not cause any problem in bleaching ability, while Sample 26 containing the known compound which is beyond the scope of the present invention undergoes marked deterioration of bleaching ability.

Further, it has been confirmed that dye images obtained by bleach-fixing treatment using Compounds 10, 4 and 12 of the present invention are by no means inferior in color density and photographic characteristics such as linearity on the characteristic curve, etc., to dye images obtained by Fuji Color Process: treatment CN-16 (color development: 3 minutes and 15 seconds, bleach: 6 minutes and 30 seconds, water wash: 2 minutes and 10 seconds, fix: 4 minutes and 20 seconds, water wash: 3 minutes and 15 seconds and stabilization: 1 minute and 5 seconds were carried out in turns, followed by drying, and each processing was carried out at 38.0±0.2° C.), and the storage stability of the dyes was excellent. As can be understood, the bleach-fixing solutions containing the compounds of the present invention are very excellent in bleach-fixing solutions.

While the invention has been described in detail and with reference to specific embodiments thereof, it will be apparent to one skilled in the art that various changes and modifications can be made therein without departing from the spirit and scope thereof.

What is claimed is:

1. A method of color photographic processing which comprises color developing an exposed silver halide color photographic light-sensitive material and thereafter carrying out a bleach treatment and a fix treatment or a bleach-fix treatment, wherein the bleaching agent used for the bleach treatment or the bleach-fix treatment is a ferric ion complex salt or a persulfate and the bleaching bath or the bleach-fixing bath or a pre-bath therefor contains at least one compound represented by the following formula (I):

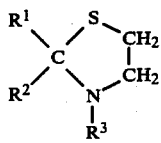

wherein $R^1$ and $R^2$ represent each a hydrogen atom, an alkyl group which may be substituted, a phenyl group which may be substituted or a heterocyclic group which may be substituted, and $R^3$ represents a hydrogen atom or a lower alkyl group which may be substituted.

2. The method of claim 1, wherein said alkyl group represented by $R^1$ and $R^2$ is a methyl group, an ethyl group or a butyl group.

3. The method of claim 1, wherein said alkyl group represented by $R^1$ and $R^2$ and said lower alkyl group represented by $R^3$ may be substituted with one or more of a hydroxyl group, a nitro group, a cyano group, a carboxyl group, a sulfonic acid group, an amino group, a halogen atom, a carbamoyl group, a sulfamoyl group, an amido group, an alkoxy group, an alkoxycarbonyl group, a carbonyloxy group, an alkoxysulfonyl group, a sulfonamide group, a sulfonyloxy group, a sulfonyl group and a heterocyclic group; and said phenyl group and said heterocyclic group for $R^1$ and $R^2$ may be substituted with one or more of an alkyl group, an aryl group, and a group as described above as a substituent on said $R^1$, $R^2$ and $R^3$.

4. The method of claim 1, wherein said heterocyclic group for $R^1$ and $R^2$ contains at least one of a nitrogen atom, an oxygen atom or a sulfur atom as a hetero atom.

5. The method of claim 4, wherein said heterocyclic group for $R^1$ and $R^2$ is selected from the group consisting of a pyridine, a thiophene, a thiazolidine, a benzimidazole, a benzothiazole, a benzoxazole, a benzotriazole, a thiazole, an imidazole and an oxazole group.

6. The method of claim 1, wherein said compound represented by the general formula (I) has the general formula (II):

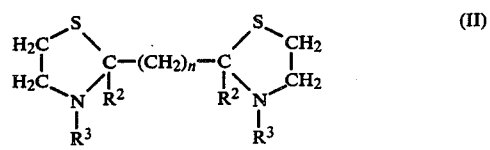

wherein $R^2$ and $R^3$, which may be the same or different, each has the same meaning as described for $R^2$ and $R^3$, respectively, in the general formula (I) and n represents 0 or an integer of 1 to 3.

7. The method of claim 1, wherein said compound represented by the general formula (I) is present in said bleaching bath in an amount of from about $1 \times 10^{-5}$ to about 1 mol per liter of processing solution.

8. The method of claim 1, wherein said compound represented by the general formula (I) is present in said bleach-fixing bath in an amount of from about $1 \times 10^{-5}$ to about 1 mol per liter of processing solution.

9. The method of claim 1, wherein said compound represented by the general formula (I) is present in said pre-bath in an amount of from about $1 \times 10^{-5}$ to about 1 mol per liter of processing solution.

10. The method of claim 1, wherein the bleaching agent is a ferric ion complex salt.

* * * * *